(12) United States Patent
de Josselin de Jong et al.

(10) Patent No.: US 6,231,338 B1
(45) Date of Patent: May 15, 2001

(54) METHOD AND APPARATUS FOR THE DETECTION OF CARIOUS ACTIVITY OF A CARIOUS LESION IN A TOOTH

(75) Inventors: Elbert de Josselin de Jong, Bussum; Eeuwe-Jan Vos, Amsterdam; Monique Harriët van der Veen, Almere, all of (NL)

(73) Assignee: Inspektor Research Systems B.V., Amsterdam (NL)

( * ) Notice: Subject to any disclaimer, the term of this patent is extended or adjusted under 35 U.S.C. 154(b) by 0 days.

(21) Appl. No.: 09/567,648

(22) Filed: May 9, 2000

(30) Foreign Application Priority Data

May 10, 1999 (NL) .................................................... 1012012

(51) Int. Cl.$^7$ .............................. A61C 1/00; A61C 3/00
(52) U.S. Cl. .............................. 433/29; 433/215; 433/229
(58) Field of Search ................................ 433/29, 215, 229

(56) References Cited

U.S. PATENT DOCUMENTS

| | | | | |
|---|---|---|---|---|
| 4,215,698 | * | 8/1980 | Nuwayser | 433/29 |
| 4,790,751 | * | 12/1988 | Reinhardt et al. | 433/29 |
| 5,040,539 | * | 8/1991 | Schmitt et al. | 433/215 X |
| 6,053,731 | * | 4/2000 | Heckenberger | 433/29 |

* cited by examiner

Primary Examiner—Nicholas D. Lucchesi
(74) Attorney, Agent, or Firm—Kinney & Lange, P.A.

(57) ABSTRACT

The invention relates to an apparatus for the detection of carious activity of a carious lesion in a tooth, comprising a light source for illuminating the tooth, and a detection device for the registration of the fluorescence radiation of the tooth. A drying device is provided for a controlled drying of the tooth. The detection device is equipped to register changes in time of the tooth's fluorescence radiation.

9 Claims, 2 Drawing Sheets

METHOD AND APPARATUS FOR THE DETECTION OF CARIOUS ACTIVITY OF A CARIOUS LESION IN A TOOTH

The invention relates to a method and apparatus for the detection of carious activity of a carious lesion in a tooth, comprising a light source for illuminating the tooth, and a detection device for the registration of the fluorescence radiation of the tooth.

Such a method and apparatus is disclosed in the American patent specification U.S. Pat. No. 4.515.476. In the known apparatus a fibre cable is connected to the light source, by means of which light of a predetermined wavelength or range of wavelengths is beamed in the direction of the tooth to be examined. Said light may be emitted by a laser source or a light source whose light is conducted through a filter. The light rays emitted by the tooth as a result of fluorescence are detected and are conducted through a further filter for the determination of the fluorescence radiation, whereby the range of wavelengths of the emitting light source is filtered out. The difference in fluorescence radiation then makes it possible to distinguish between the portions of teeth that are affected by carious lesion and the portions of teeth that are healthy.

It is indeed possible to identify and detect carious lesions by means of the apparatus mentioned in the preamble, however, a problem of the known apparatus is that it does not provide any information on whether it is a carious lesion that requires treatment. The person skilled in the art is aware of the fact that caries starts as demineralization of the surface of the tooth which may progressively lead to discolouring of the surface of the tooth, to its softening, and finally, to the development of a cavity. At the moment the carious lesion is discovered, either with or without the application of the apparatus disclosed in U.S. Pat. No. 4.515.476, it is not known whether a quickly developing demineralization or a slow process of demineralization and remineralization is involved. The type and the nature of the lesion determine the desired method of treatment. As mentioned just now, a carious lesion may recover as a result of remineralization. Therefore, if the detected lesion is one that is already provided with a remineralized coating, an adapted and less extensive treatment will suffice.

It is the object of the invention, to provide an apparatus as referred to in the preamble, with which it is possible in a very short time, and in any case, during a visit at the dentist's, to determine whether the examined lesion is an active lesion without coating, or an inactive lesion already provided with a remineralized coating. On this basis the correct method of treatment can then be selected.

To this end the apparatus according to the invention is characterized, in that a drying device is provided for a controlled drying of the tooth and in that the detection device is equipped to register changes in time of the tooth's fluorescence radiation. It has been shown that drying the tooth changes the fluorescence radiation. Drying and the resulting water loss causes the fluorescence radiation of the tooth to decrease, showing the difference between the healthy portion of the tooth and the portion of the tooth affected by carious lesion. It has been shown, that an active lesion loses more water and dries more quickly than healthy enamel, while an inactive lesion that is provided with a remineralized surface coating, dries more slowly, so that the apparatus according to the invention thus provides means by which the nature and severity of the lesion can be determined.

In one preferred embodiment the apparatus according to the invention is characterized, in that the detection device is equipped to register the curve of the fluorescence radiation in relation to the operational duration of the drying appliance. This provides an accurate picture of the curve of the tooth's fluorescence radiation, and consequently of the nature and severity of the carious lesion, due to the fact that the difference can be seen in the effect that a particular drying process has on the examined tooth.

The apparatus may be designed such that in order to obtain personalized results, first a calibration is carried out on healthy tooth enamel of the person examined by drying the enamel with the drying appliance and simultaneously determining and storing the curve of fluorescence radiation with the detection device. Then a similar operation can be carried out on the carious lesion to determine its carious activity.

In the apparatus according to the invention it is, however, preferred that the drying appliance and the detection device be equipped for the simultaneous drying of a first tooth portion having a carious lesion and a second tooth portion that is lesion-free, and for the simultaneous registration of the curve in time of the fluorescence radiation of the first and the second tooth portion. This makes it possible to further reduce the measuring time required for the determination of carious activity of the examined tooth.

It is possible to allow the drying operation of the tooth to occur by natural loss of moisture in the atmosphere. However, according to the invention it is preferred that a drying appliance be provided that carries out the drying operation of the examined tooth in a controlled manner, for example, by supplying a constant air flow of a predetermined volume per minute. The controlled drying may be simply carried out such that the operational duration of the drying appliance is set at a predetermined value.

In another aspect of the invention the apparatus is characterized, in that the operational duration of the drying appliance depends on the extent to which the fluorescence radiation of a tooth portion that is lesion free, changes. This avoids the tooth enamel being subjected to extensive drying, which could have an adverse effect on the quality of the tooth enamel.

In a further aspect of the invention the apparatus is characterized, in that the detection device is equipped to determine the ratio r of the fluorescence radiation of the first and the second tooth portion, and for the registration of the curve of said ratio r in time to indicate the lesion and the nature of the lesion. Therefore, a very suitable embodiment is characterized, in that the detection device is equipped to determine the time derivative of the ratio r, and in that the apparatus is further provided with an indicator for, subject to said derivative, indicating whether the lesion is active or inactive. This is a simple manner of establishing the quality of the examined carious lesion. Because the ratio r becoming an active lesion without a remineralized surface coating is—within the operational duration of the drying appliance—at an undetermined minimum, its determination provides a good indication of the respective carious activity.

In yet another aspect of the invention the apparatus is characterized, in that the detection device is equipped for the determination of the halftime of the fluorescence radiation of the first and second tooth portion, and in that the apparatus is further provided with an indicator for indicating, subject to the a half times, whether the lesion is active or inactive. This halftime provides the clear indication of the quality of the enamel, and the nature of the possibly present lesion.

The invention is also embodied in a method for the determination of carious activity of a carious lesion in a tooth, wherein the tooth is illuminated, and the fluorescence radiation of the tooth is detected, and which is characterized, in that the tooth is subjected to drying and that the change in time of the fluorescence radiation of the tooth is registered.

The invention will now be elucidated with reference to the drawings, in which

Figure 1:
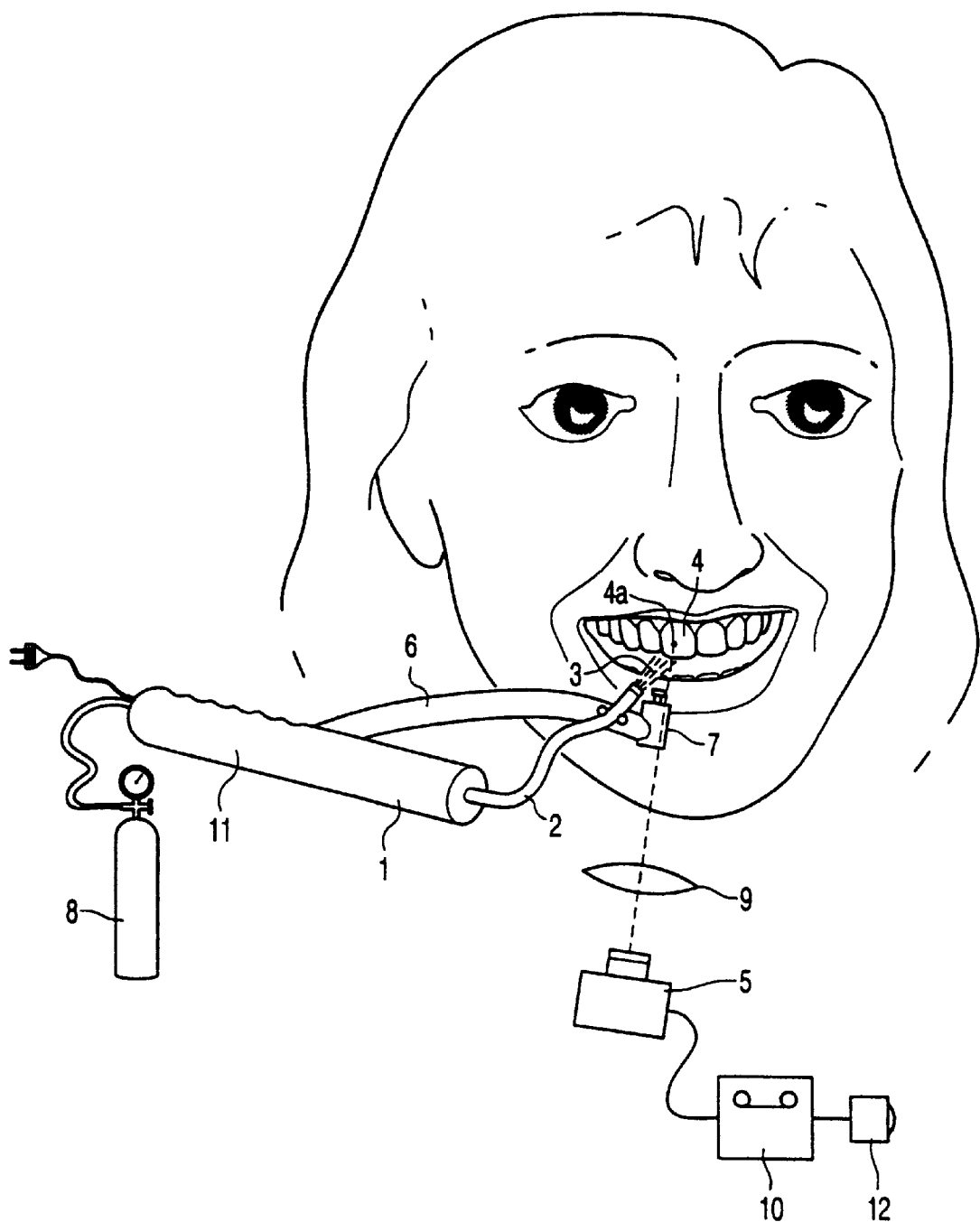
FIG. 1, shows the apparatus according to the invention during use.

FIG. 1 shows that the apparatus for the determination of carious activity of a carious lesion 4a in a tooth 4 comprises a light source, in this case the laser 1, for the illumination of the tooth 4 via a fibre strand 2 connected to the laser 1. Optionally, another light source may be used, for example, an arc lamp, wherein the light is conducted through a strip-guide filter for obtaining light of a specific range of wavelengths, for example blue-violet light. Further, a drying appliance 6, 7, 8 is provided for the controlled drying of the tooth 4. To this end a tube 6 is connected to an air cylinder 8, by means of which via a nozzle 7 a controlled amount of air can be directed onto the tooth 4 for drying.

The invention is also equipped with a detection device 5, 9,10 for the registration of the fluorescence radiation of the tooth 4. The detection device 5, 9, 10 has a light filter 9 which blocks the light from the laser source 1, but which lets through the light of a predetermined wavelength that is relevant for the determination of the fluorescence radiation of the tooth 4. The detection device 5, 9, 10 further comprises a camera 5, and more specifically a CCD camera connected to a computer 10, by means of which the registered images can be digitally stored and processed further. To allow measurement of the fluorescence radiation of both the healthy portion of the tooth 4 and the lesion 4a within a few seconds, the tooth 4 is dried with the drying appliance 6, 7, 8 using a continuous airflow of a predetermined volume per minute. The supply tube 6 for the drying air may be incorporated in a handgrip 11, with which also the light source 1 is operated.

In the embodiment of the apparatus according to the invention shown, the drying appliance 6, 7, 8 is active at the same time as the detection device 5, 9, 10 for the simultaneous drying of the tooth 4 comprising the lesion 4a and the registration of the curve in time of the fluorescence radiation of the healthy portion of the tooth 4 and of the lesion 4a. Preferably, the operational duration of the drying appliance 6, 7, 8 in operation is pre-set.

In another preferred embodiment the operational duration of the drying appliance 6, 7, 8 in operation depends on the measure of change in fluorescence radiation of the healthy portion of the dental enamel of the tooth 4. The detection device 5, 9, 10 is further equipped for the registration of the curve of the fluorescence radiation subject to the operational duration of the drying appliance 6, 7, 8. Using the apparatus according to the invention, the relative fluorescence radiation of the lesion 4a compared with the fluorescence radiation of the remaining healthy enamel of the tooth 4 is determined as time function which, as already mentioned, is a measure for the extent to which the tooth 4 and the respective lesion 4a, is dried.

The detection device 5, 9, 10 is further preferably equipped such that the ratio r of the fluorescence radiation of the lesion 4a and of the healthy enamel 4 is determined, whereafter the quality of the lesion is most simply established by a subsequent determination of the time derivative of the ratio r while the drying appliance 6, 7, 8, is in operation; the apparatus being provided with an indicator 12 for indicating, subject to said derivative, whether the lesion 4a is active or inactive. If the minimum value of the curve of the ratio of the fluorescence radiation is not limited by a boundary, and therefore the derivative of the ratio equals zero, the lesion is an active one, that is to say a lesion without remineralized surface coating. In the event that no true minimum can be determined, the lesion is an inactive one.

Alternatively, instead of determining the derivative, the halftime of the fluorescence radiation of the lesion and of the healthy enamel may be determined in order to establish whether a lesion is involved, and the nature of the lesion.

FIG. 1, is a schematic representation of the measurement of the light radiating from the tooth 4. In practice this can be done, for example, by conducting the light radiating from the tooth via a fibre to a photodiode, with a filter being placed in the path of said detection light. Concerning the measurements to be carried out on the tooth 4, this, in contrast with the elucidated example where this is done on the healthy enamel and the enamel with a lesion simultaneously, may also be carried out sequentially in order to first provide a calibration point by measuring the healthy enamel, whereafter the curve of the fluorescence radiation profile for the portion of the tooth 4 having the lesion is determined in the manner explained above.

Figure 2:
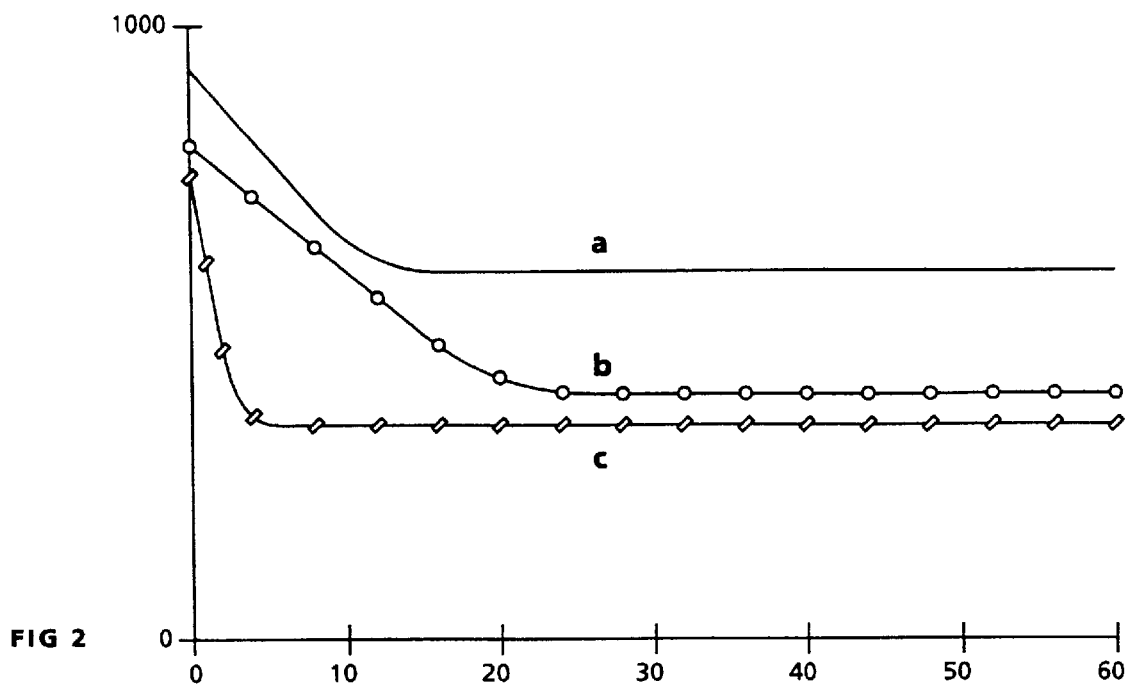
FIG. 2, shows the curve of fluorescence radiation in an exemplary case of healthy enamel and of an active and inactive lesion.
Figure 3:
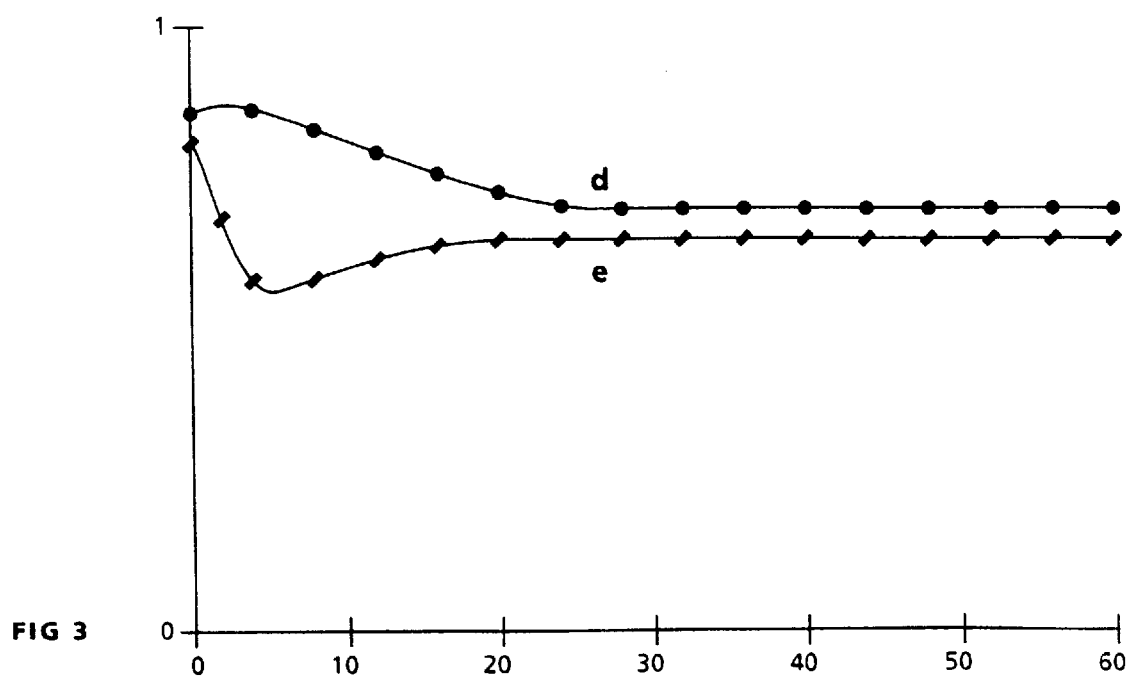
FIG. 3, shows the curve of the ratio of the fluorescence radiations of an active and inactive lesion compared with healthy enamel.

In the FIGS. 2 and 3 the time in seconds is plotted on the x-axis. In FIG. 2, the y-axis shows the level of fluorescence radiation, while in FIG. 3, on the y-axis a proportional Figure is given corresponding with the ratio of the fluorescence radiation of the lesion compared with the fluorescence radiation of the healthy enamel.

FIG. 2, shows a graph of the curve of healthy enamel, graph b shows the fluorescence radiation curve of an inactive lesion, and graph c that of an active lesion. Clearly the rate reduction in the fluorescence radiation curve of an active lesion is significantly greater than that of healthy enamel and that of an inactive lesion. With regard to the curve of the illustrated fluorescence radiation it should be noted that this is a typical exemplary case, and that the respective final value of the fluorescence radiation may differ from those in the illustrated case. This also applies to the starting values and the rate and the extent to which the fluorescence radiations change.

FIG. 3, shows the relationship between the fluorescence radiation curves of the active and inactive lesion, each time calibrated to the curve of the fluorescence radiation of the healthy enamel. Graph d shows the curve of the respective ratio of the inactive lesion, while graph e shows the curve of the active lesion. This Figure clearly shows that the curve of the ratio of the inactive lesion is substantially on a steady decline, whereas the ratio of the active lesion in the operational phase of the drying appliance is at an undetermined minimum so that the derivative of this ratio curve is therefore zero. This facilitates a simple and quick identification of the quality of the lesion by determining the minimum value of the ratio curve.

It will be clear to the person skilled in the art that the above elucidation of the invention is not limitative, and that numerous variations on the theme are possible within the frame of the invention, all of which within the scope of the appended claims.

What is claimed is:

1. An apparatus for detection of carious activity of a carious lesion in a tooth, comprising:

a light source for illuminating the tooth;

a detection device for registration of fluorescence radiation of the tooth; and a drying device for a controlled drying of the tooth; wherein the detection device is equipped to register changes in time of the fluorescence radiation of the tooth.

2. An apparatus according to claim 1, wherein the detection device is equipped to register a curve of the fluorescence radiation in relation to an operational duration of the drying device.

3. An apparatus according to claim 1, wherein the drying device and the detection device are equipped for simultaneous drying of a first tooth portion having a carious lesion and a second tooth portion that is lesion-free, and for simultaneous registration of a curve in time of the fluorescence radiation of the first and the second tooth portion.

4. An apparatus according to claim 1, wherein the drying device has an operational duration in operation which is pre-set.

5. An apparatus according to claim 1, wherein the drying device has an operational duration which depends on the extent to which the fluorescence radiation, as detected by the detection device from a tooth portion that is lesion-free, changes.

6. An apparatus according to claim 1, wherein the detection device is equipped to determine a ratio r of fluorescence radiation of a first tooth portion having a carious lesion and a second tooth portion that is lesion-free, and for registration of a curve of said ratio r in time to indicate the lesion and nature of the lesion.

7. An apparatus according to claim 6, wherein the detection device is equipped to determine a time derivative of the ratio r, and further comprising:

an indicator for, subject to said determined time derivative, indicating whether a lesion is active or inactive.

8. An apparatus according to claim 1, wherein the detection device is equipped for determination of halftimes of fluorescence radiation of a first tooth portion having a carious lesion and a second tooth portion that is lesion-free, and further comprising:

an indicator for indicating, subject to the determined halftimes, whether a lesion is active or inactive.

9. A method for determination of carious activity of a carious lesion in a tooth, comprising:

illuminating a tooth;

driving the illuminated tooth;

detecting fluorescence radiation of the illuminated tooth during drying; and registering a change in time of the detected fluorescence radiation of the tooth.

* * * * *